# (12) United States Patent
Duve

(10) Patent No.: US 8,486,276 B2
(45) Date of Patent: Jul. 16, 2013

(54) METHOD OF TREATING WATER AND AQUEOUS SYSTEMS IN PIPES WITH CHLORINE DIOXIDE

(75) Inventor: Hans Duve, Duelmen (DE)

(73) Assignee: Infracor GmbH, Marl (DE)

( * ) Notice: Subject to any disclaimer, the term of this patent is extended or adjusted under 35 U.S.C. 154(b) by 281 days.

(21) Appl. No.: 12/642,201

(22) Filed: Dec. 18, 2009

(65) Prior Publication Data

US 2010/0155341 A1    Jun. 24, 2010

(30) Foreign Application Priority Data

Dec. 19, 2008   (DE) .................. 10 2008 055 016

(51) Int. Cl.
*C02F 1/76* (2006.01)

(52) U.S. Cl.
USPC ........... 210/754; 210/758; 210/764; 210/192; 423/477

(58) Field of Classification Search
USPC ............. 210/753–756, 758, 764, 167.3, 192, 210/198.1, 205, 209, 220, 232, 234, 236, 210/241; 423/477; 239/587.1
See application file for complete search history.

(56) References Cited

U.S. PATENT DOCUMENTS

| | | | |
|---|---|---|---|
| 4,013,761 A | 3/1977 | Ward et al. | |
| 4,019,983 A | 4/1977 | Mandt | |
| 4,082,900 A * | 4/1978 | Shimogori et al. | ........... 422/241 |
| 4,104,190 A | 8/1978 | Hartshorn | |
| 4,210,534 A | 7/1980 | Molvar | |
| 4,247,531 A | 1/1981 | Hicks | |
| 4,250,144 A | 2/1981 | Ratigan | |
| 4,251,224 A | 2/1981 | Cowley et al. | |
| 4,287,054 A | 9/1981 | Hollingsworth | |
| 4,414,193 A | 11/1983 | Fredette et al. | |
| 4,534,952 A | 8/1985 | Rapson et al. | |
| 4,618,479 A | 10/1986 | Santillie et al. | |

(Continued)

FOREIGN PATENT DOCUMENTS

| | | |
|---|---|---|
| DE | 1 069 122 | 11/1959 |
| DE | 1 203 691 | 10/1965 |

(Continued)

OTHER PUBLICATIONS

Definition of "appliance" from yourdictionary.com (obtained Nov. 2010).*

(Continued)

*Primary Examiner* — Lucas Stelling
(74) *Attorney, Agent, or Firm* — Oblon, Spivak, McClelland, Maier & Neustadt, L.L.P.

(57) ABSTRACT

The present invention relates to a method of treating water and an aqueous system, situated in a pipe, with chlorine dioxide ($ClO_2$), the method including generating $ClO_2$ in a reaction space such that the generated $ClO_2$ is completely surrounded by a system to be treated, and delivering the $ClO_2$ generated in the reaction space to the system to be treated which is situated in the pipe, wherein the system surrounding the reaction space is the system to be treated, the reaction space is a component of a mobile device and the mobile device can be introduced into the pipe, in which the system to be treated is situated, and removed again independently of the pressure state of the pipe containing the system to be treated, and the reaction space is situated in the pipe containing the system to be treated.

17 Claims, 3 Drawing Sheets

U.S. PATENT DOCUMENTS

| | | |
|---|---|---|
| 4,820,408 A | 4/1989 | Sandig |
| 5,120,452 A | 6/1992 | Ness et al. |
| 5,204,081 A | 4/1993 | Mason et al. |
| 5,227,306 A | 7/1993 | Eltomi et al. |
| 5,290,524 A | 3/1994 | Rosenblatt et al. |
| 5,318,702 A | 6/1994 | Ashbrook |
| 5,324,497 A | 6/1994 | Westerlund |
| 5,382,520 A | 1/1995 | Jenson et al. |
| 5,435,913 A | 7/1995 | Ashbrook |
| 5,458,858 A | 10/1995 | Dawkins |
| 5,565,182 A | 10/1996 | Sokol |
| 5,651,996 A | 7/1997 | Roozdar |
| 5,865,537 A | 2/1999 | Streiff et al. |
| 5,993,669 A | 11/1999 | Fulmer |
| 6,051,135 A | 4/2000 | Lee et al. |
| 6,083,457 A | 7/2000 | Parkinson et al. |
| 6,325,970 B1 | 12/2001 | Parkinson et al. |
| 6,436,345 B1 | 8/2002 | Roensch et al. |
| 6,468,479 B1 | 10/2002 | Mason et al. |
| 6,497,822 B2 | 12/2002 | Blanchette et al. |
| 6,645,457 B2 | 11/2003 | Mason et al. |
| 6,716,354 B2 | 4/2004 | Rosenblatt et al. |
| 6,761,872 B2 | 7/2004 | Roensch et al. |
| 6,767,470 B2 | 7/2004 | Iverson et al. |
| 6,790,427 B2 | 9/2004 | Charles et al. |
| 6,982,040 B2 | 1/2006 | Costa et al. |
| 7,011,751 B1 | 3/2006 | Waldner et al. |
| 7,077,995 B2 | 7/2006 | Roensch et al. |
| 7,094,353 B2 | 8/2006 | Unhoch |
| 7,147,786 B2 | 12/2006 | Costa et al. |
| 7,186,376 B2 | 3/2007 | Iverson et al. |
| 7,220,367 B2 | 5/2007 | Speronello et al. |
| 7,255,797 B2 | 8/2007 | Martin |
| 7,261,821 B2 | 8/2007 | Beardwood |
| 7,285,255 B2 | 10/2007 | Kadlec et al. |
| 7,320,761 B2 | 1/2008 | Costa et al. |
| 7,326,352 B2 | 2/2008 | Waldner et al. |
| 7,449,119 B2 | 11/2008 | Brown |
| 7,452,511 B2 | 11/2008 | Schmitz et al. |
| 7,571,676 B2 | 8/2009 | Nelson et al. |
| 7,575,673 B2 | 8/2009 | Unhoch |
| 7,713,501 B2 | 5/2010 | Priegel |
| 7,744,765 B2 | 6/2010 | Bjerkan et al. |
| 7,754,082 B2 | 7/2010 | Speece et al. |
| 7,906,016 B2 | 3/2011 | Weber et al. |
| 2003/0138371 A1 | 7/2003 | McWhorter et al. |
| 2004/0101438 A1 | 5/2004 | Nelson et al. |
| 2004/0175322 A1 | 9/2004 | Woodruff et al. |
| 2004/0256330 A1 | 12/2004 | Okazaki |
| 2005/0155936 A1 | 7/2005 | Martin et al. |
| 2006/0016765 A1 | 1/2006 | DiPietro et al. |
| 2006/0120945 A1 | 6/2006 | Warner et al. |
| 2007/0034570 A1 | 2/2007 | DiMascio |
| 2007/0272622 A1 | 11/2007 | Mercer et al. |
| 2008/0006586 A1 | 1/2008 | Axtell et al. |
| 2008/0217258 A1 | 9/2008 | Buchan |
| 2009/0159538 A1 | 6/2009 | Duve |
| 2009/0173697 A1 | 7/2009 | Axtell et al. |
| 2009/0246074 A1 | 10/2009 | Nelson et al. |
| 2010/0006513 A1 | 1/2010 | Fishler et al. |
| 2010/0074813 A1 | 3/2010 | Dee |
| 2010/0086623 A1 | 4/2010 | Doona et al. |
| 2010/0155341 A1 | 6/2010 | Duve |

FOREIGN PATENT DOCUMENTS

| | | |
|---|---|---|
| DE | 23 43171 A1 | 3/1975 |
| DE | 102 25 626 A1 | 12/2003 |
| DE | 20 2004 005 755 U1 | 8/2004 |
| DE | 103 26 628 A1 | 1/2005 |
| DE | 10 2006 060 578 A1 | 6/2008 |
| EP | 0 119 686 A1 | 9/1984 |
| EP | 0 766 996 A1 | 4/1997 |
| EP | 0 866 031 A1 | 9/1998 |
| EP | 0 881 985 | 12/1998 |
| EP | 1 504 767 A1 | 2/2005 |
| GB | 2 155 459 A | 9/1985 |
| IT | 1351156 | 1/2009 |
| JP | 2002-220207 | 8/2002 |
| JP | 2003-170029 | 6/2003 |
| JP | 2008-94662 | 4/2008 |
| NL | 9300747 | 12/1993 |
| RU | 45378 U2 | 4/2000 |
| RU | 2163882 C2 | 4/2000 |
| WO | WO 97/30931 | 8/1997 |
| WO | WO 2004/078648 A1 | 9/2004 |
| WO | WO 2005/087657 A1 | 9/2005 |
| WO | WO 2007/029183 A2 | 3/2007 |
| WO | WO 2008/116724 A1 | 10/2008 |
| WO | WO 2009/077160 A1 | 6/2009 |
| WO | WO 2009/077213 A1 | 6/2009 |
| WO | WO 2009/077309 A1 | 6/2009 |
| WO | WO 2010/069632 A1 | 6/2010 |

OTHER PUBLICATIONS

U.S. Appl. No. 12/734,877, filed Jun. 1, 2010, Belluati, et al.
U.S. Appl. No. 13/109,508, filed May 17, 2011, Duve.
"Disinfectants", Scientific and Research Institute for Technical and Economic Research in Chemical Industry, Survey Information, ISSN 0203-7971, 1986, 3 pages (English Translation).
U.S. Appl. No. 13/641,576, filed Oct. 16, 2012, Duve.

* cited by examiner

METHOD OF TREATING WATER AND AQUEOUS SYSTEMS IN PIPES WITH CHLORINE DIOXIDE

BACKGROUND OF THE INVENTION

1. Field of the Invention

The invention relates to a method of treating water and aqueous systems (hereinafter called the systems to be treated) in pipes with chlorine dioxide ($ClO_2$).

2. Discussion of the Background

Chlorine dioxide can be used in water treatment and for treating aqueous systems because of its high bactericidal, virucidal and algicidal activity. Aqueous systems are used in a multiplicity of industrial processes such as, in the food industry, in brewing processes, in the drink industry and in paper making, inter alia, as transport medium, as heating and cooling medium and for washing purposes. The transport of such aqueous systems typically proceeds primarily in pipes. Generally, biological growth in these systems can be restricted by using biocides such as, chlorine dioxide. Owing to the explosive tendency of gaseous chlorine dioxide (c>300 g/m³) and chlorine dioxide solutions (c>26 g/l), chlorine dioxide cannot be stored in compressed form or in solutions of relatively high concentration. Owing to these chemical properties, chlorine dioxide is typically produced at the point of use. Such point-of-use production is achieved by mixing basic chemicals in special reactors of chlorine dioxide generation systems. The chemical storage vessels, the metering appliances and also the reactor of the chlorine dioxide systems form a locally linked apparatus which is generally erected in rooms accessed by people.

There are a plurality of methods, but principally three underlying methods (see below), for synthesizing $ClO_2$ which have typically been used commercially for water treatment. These methods use sodium chlorite ($NaClO_2$) as one of the starting materials. The underlying chemistry of the three methods is explained hereinafter. The substances used in these methods are referred to as starting chemicals or reactants.

1. Method Using Sodium Chlorite and Strong Acid

In the first method, a strong acid is used together with sodium chlorite. The strong acid is usually hydrochloric acid or sulphuric acid. When hydrochloric acid is used, the reaction stoichiometry is as follows:

$$5NaClO_2 + 4HCl \rightarrow 4ClO_2 + 5NaCl + 2H_2O.$$

In addition, chlorine dioxide can be formed with the use of sulphuric acid in accordance with the following reaction:

$$10NaClO_2 + 5H_2SO_4 \rightarrow 8ClO_2 + 5Na_2SO_4 + 2HCl + 4H_2O.$$

2. Method Using Sodium Chlorite and Chlorine

This method uses gaseous chlorine together with sodium chlorite. The reaction proceeds in two stages, first with the formation of hydrochloric acid as follows:

$$Cl_2 + H_2O \rightarrow HOCl + HCl.$$

Then the intermediate, hypochloric acid (HOCl), reacts with sodium chlorite, forming chlorine dioxide ($ClO_2$) as follows:

$$HOCl + HCl + 2NaClO_2 \rightarrow 2ClO_2 + 2NaCl + H_2O.$$

The stoichiometric reaction from the two above equations is:

$$Cl_2 + 2NaClO_2 \rightarrow 2ClO_2 + 2NaCl.$$

3. Method Using Sodium Chlorite and Sodium Hypochlorite

In the third method, sodium hypochlorite (NaOCl) is used together with sodium chlorite in accordance with the following reactions:

$$NaOCl + HCl \rightarrow NaCl + HOCl, \text{ and}$$

$$HCl + HOCl + 2NaClO_2 \rightarrow 2ClO_2 + 2NaCl + H_2O.$$

The synthesis reactions for generating chlorine dioxide are generally carried out in reactors which are operated either continuously or by the batch method.

Two explosion limits must be taken into account in the generation of chlorine dioxide:
(A) with respect to contact with air, the explosion limit of concern is more than 6 g of $ClO_2$/l of solution, and
(B) with respect to spontaneous autodecomposition, the explosion limit of concern is more than 26 g of $ClO_2$/l of solution.

For example, in the case of the chlorine dioxide syntheses carried out by methods 1 to 3, when use is made of starting chemicals which would lead to, in the reaction space, a concentration of greater than approximately 26 g of $ClO_2$/l of solution, dilution water is added to the reaction space in order to bring the concentration below that of spontaneous autodecomposition. When the chlorine dioxide solution leaving the reaction space contains 20 g of $ClO_2$/l or less, which is typical, the solution is diluted with a further water stream to a concentration of roughly less than 3 g of $ClO_2$/l of solution.

In order for these methods 1 to 3 to be operated with satisfactory results with respect to plant safety, chlorine dioxide yield and time-specific production rate, a variety of processing variations are typically performed:

Installation and use of metering points on the pipe having systems to be treated for addition of chlorine dioxide generated outside the pipe.

Use of diluted starting chemicals such that respective concentrations of the chlorine dioxide solution produced fall below 26 g/l or 6 g/l.

Generation of reduced pressure in the reactor by applying a vacuum in order to obtain reduction of the chlorine dioxide concentration in the gas phase to <300 g/m³.

Generation of reactor overpressure (e.g., by using pressure-retention valves at the reactor outlet) to prevent the formation of a gas phase by exceeding the solubility limit of chlorine dioxide and to increase the yield.

Use of batch methods having long reaction times in order to increase the yield when diluted starting chemicals are used.

Use of superstoichiometric acid amounts in the chlorite/acid method and use of superstoichiometric chlorine amounts in the chlorite/chlorine method to increase the yield.

Despite the use of the above-mentioned procedures, in the event of incorrect operation of the chlorine dioxide generation systems (e.g., due to loss of dilution water or by failure of the pressure control) spontaneous decomposition (explosion) of chlorine dioxide can occur, or chlorine dioxide may, owing to leakage or breakage of separation surfaces between the chlorine-dioxide-containing solution and the environment, lead to hazards in the surroundings of the generation systems. The use of diluted starting chemicals, which can lead to chlorine dioxide solutions with a concentration of less than 6 g/l and therefore sacrifice the relatively high time-specific generation rates of the chlorine dioxide systems, also cannot prevent the hazard to the surroundings of the generation systems wherein the MAK value (maximum workplace concentration) of 0.1 ppm is exceeded in the event of incorrect operation. In order to minimize these hazards, various measures have been typically implemented at the generation systems themselves, and also at the sites where the chlorine dioxide generation systems are erected. For example, complex servicing work on the generation systems including regular replacement of the reactors, spatially isolating erection sites for the generation systems, and forcing aeration and air monitoring of the atmosphere of the erection site by continuous gas analyses are usually needed.

After production of the chlorine-dioxide-containing solutions, the solutions are generally transported into pipes using pressure elevation appliances. This takes place, for example, via connection ports which are situated in the pipe. The metering line for the chlorine-dioxide-containing solution, which extends into the pipe having the systems to be treated, can only be worked on after clearance of the pipe. Clearance in this case means depressurizing and emptying the system-bearing pipe. The points for chlorine dioxide addition are frequently in bypass lines which are provided with shutoff elements upstream and downstream of the addition site.

BRIEF DESCRIPTION OF THE DRAWINGS

FIG. 2a represents a maintenance state. FIG. 2b represents an operating state.

Figure 1:
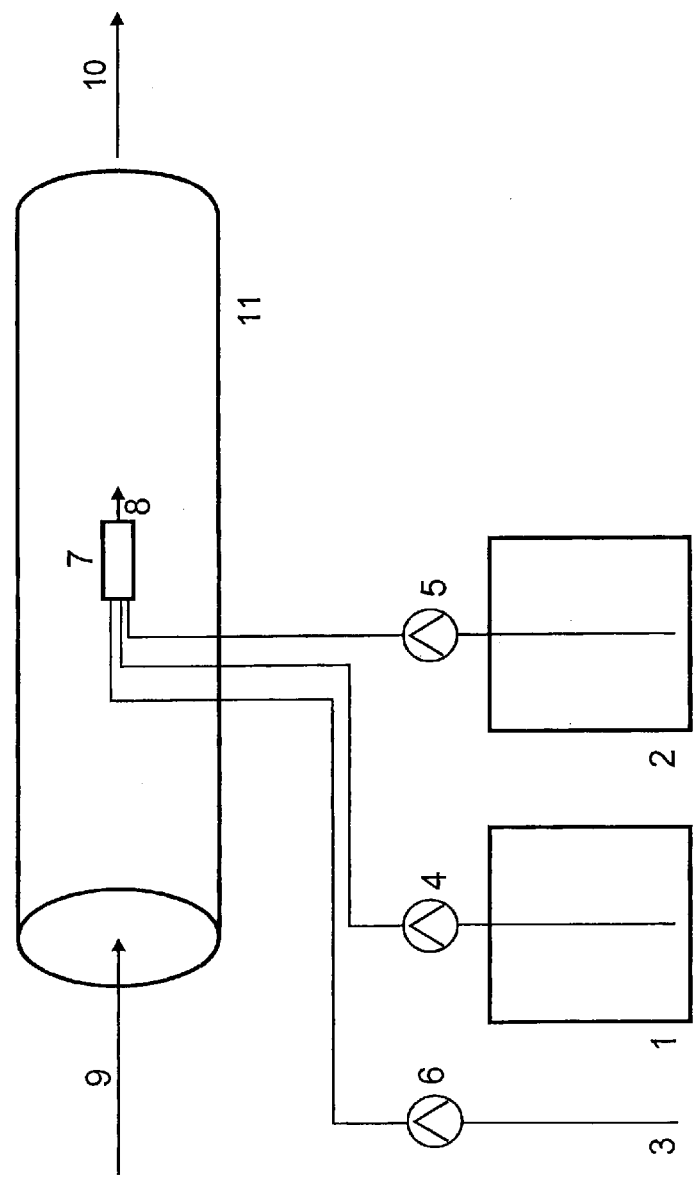
FIG. 1 illustrates a structure for carrying out the method having a reaction space in a pipe without the mobile device and without being restricted to certain starting chemicals (reactants) or embodiments.
Figure 2B:
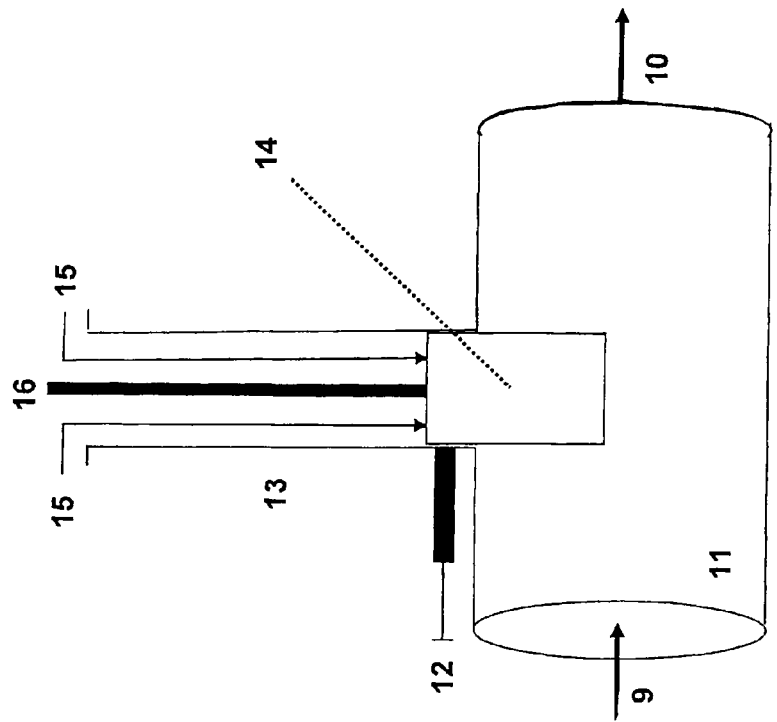
FIGS. 2a and 2b illustrate a preferred device for carrying out the method according to the present invention.
Figure 2A:
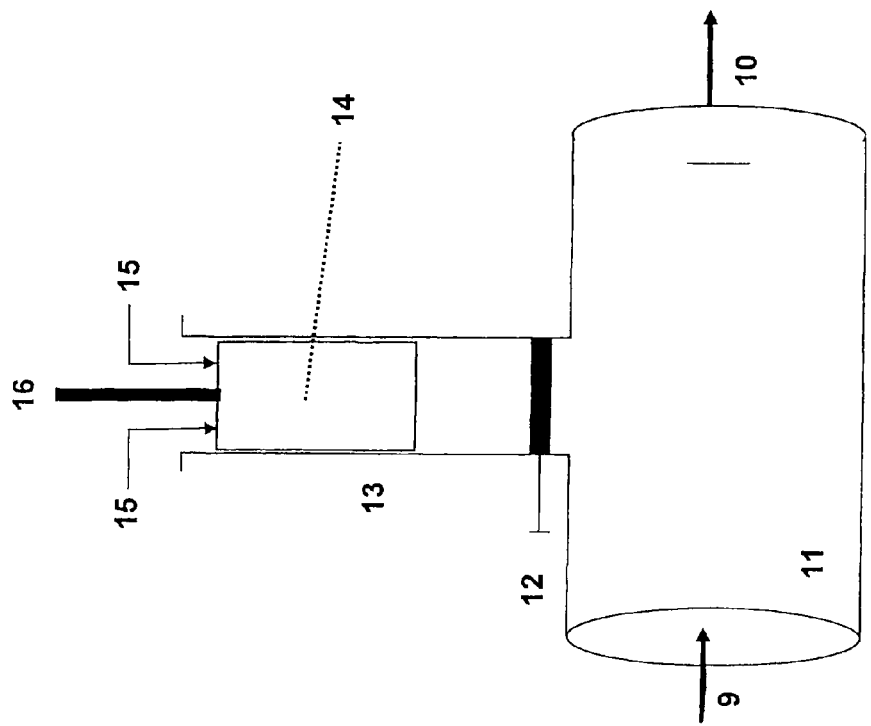

LEGEND TO FIG. 1, FIG. 2a AND FIG. 2b

1 Chlorite storage tank
2 Acid storage tank
3 Water connection
4 Chlorite feed pump
5 Acid feed pump
6 Dilution water feed pump
7 Reaction space (reactor)
8 Reaction space outlet (reactor outlet)
9 System to be treated
10 Treated system
11 Pipe
12 Shutoff element
13 Guide channel
14 Mobile device
15 Reactant feed lines
16 Movement device

DETAILED DESCRIPTION OF THE PRESENT INVENTION

It is therefore an object of the present invention to provide a safer and more efficient method of treating water and aqueous systems which are situated in pipes with chlorine dioxide. More specifically, it is an object of the present invention to minimize the hazard potential of these types of treatments while simultaneously reducing the cost expenditure on safety installations. In addition, it is another object of the present invention that all necessary process steps be able to be carried out independently of the pressure state of the pipe which contains the system to be treated.

It is yet another object of the present invention to provide a safer treatment method for both the environment (e.g., avoiding emission of $ClO_2$ into the environment) and people (e.g., avoiding emission of $ClO_2$ into the spaces in which the plant is customarily operated). Finally, it is an object of the present invention to provide a treatment method that can take advantage of the benefits resulting from the use of concentrated starting chemicals (e.g., reduced material transport, higher reaction rate, higher yields, and lower reactor volume), while at the same time allowing the necessary assembly and maintenance work to be carried out independently of the pressure state of the system-bearing pipe.

The present invention relates to a method of treating water and an aqueous system, situated in a pipe, with chlorine dioxide ($ClO_2$), said method comprising generating $ClO_2$ in a reaction space such that the generated $ClO_2$ is completely surrounded by a system to be treated, and delivering the $ClO_2$ generated in the reaction space to the system to be treated which is situated in the pipe, wherein the system surrounding the reaction space is the system to be treated, the reaction space is a component of a mobile device and the mobile device can be introduced into the pipe, in which the system to be treated is situated, and removed again independently of the pressure state of the pipe containing the system to be treated, and the reaction space is situated in the pipe containing the system to be treated.

The present inventors have surprisingly found that the above objects were achieved by the above- and below-described methods.

The above described features of the present invention enables safe working by avoiding the escape of $ClO_2$ into working rooms or the environment and eliminates adverse consequences of explosive decompositions. It should be noted that the reaction space is a component of a mobile device which can be brought into the pipe and removed again independently of the pressure state thereof. The reaction space in which the $ClO_2$ is generated is a component of a mobile device and after introduction into the pipe can be completely surrounded by water or an aqueous system and this is simultaneously the system to be treated. This shifting of the point of formation of the chlorine dioxide out of spaces accessed by people and the storage site of the starting chemicals significantly increases safety. Thus, leaks and explosions of the reaction space can be virtually neutralized by the large volume of the systems to be treated.

The reaction space can be introduced into a pressurized pipe through which a system to be treated flows, and can be removed from this pipe again without interrupting the transport and therefore the utilization in the pipe of the system to be treated. In addition, the reaction space is preferably in the main pipe of the system to be treated and not in a bypass line to the main line which can be spatially isolated by shutoff elements situated upstream and downstream of the site in the bypass line for feeding chlorine dioxide to the system to be treated.

Some particular advantages of the present invention will be described in more detail hereinafter.

Chlorine dioxide can be added to a system to be treated which is situated in a pipe at any position and at any pressure state of the pipe. A leak of the reaction space, in particular of the reactor, which is situated in a pipe can be handled simply and safely in the system to be treated which is flowing past the wall thereof. The chlorine dioxide, in particular, exiting in the event of a leak of the reaction space is diluted to a non-critical concentration and transported away. The same applies to any starting chemicals exiting from the reaction space, in particular the reactor. Since the synthesis of chlorine dioxide from concentrated starting chemicals can proceed without dilution by water, the necessary superstoichiometric yield-increasing excess amounts of acid and/or chlorine can be decreased and additionally there is a significant increase in reaction rate, a high specific generation output of the reaction space results. Furthermore, by reducing the necessary median residence time of the reactants in the reaction space there is the possibility of minimizing the reaction space volume, as a result of which, e.g., the installation of the reaction space, in particular the reactor, into a pipe through which the system to be treated flows becomes possible.

In addition, from a safety point of view, there can be an improvement of the ratio between the amount of chlorine dioxide permanently present during synthesis in the reaction space and the amount of system to be treated.

Also, shifting the point of production of the chlorine dioxide out of the spaces accessed by people and out of the storage site of the starting chemicals can significantly increases safety. Reaction space leaks and reaction space explosions can be virtually neutralized by the large volume of system to be treated relative to the amount of chlorine dioxide which is present in the reaction space. Preferably the site of addition of the chlorine dioxide to the system to be treated is not situated in a bypass line to the main line of the system to be treated which can be spatially isolated by shutoff elements situated upstream and downstream of the site of addition situated in the bypass line, but directly in the main line. By this means, incorrect addition of chlorine dioxide into a space having restricted volume and without replacement of the system to be treated (space isolated by shutoff elements), the resultant hazards can be safely prevented. The high flexibility of the method according to the present invention can significantly expand the fields of application of chlorine dioxide treatment and, in addition, can simultaneously reduce industrial expenditure for treatment of systems in pipes.

Accordingly, the above-described features of the present invention, in addition to potential flexibility of a biocide treatment method, permits safe working, even with the use of concentrated starting chemicals, by avoiding the escape of $ClO_2$ into working rooms or the environment and can eliminate the adverse consequences of explosive decompositions.

The reaction space in which the $ClO_2$ is generated can be completely surrounded by the systems to be treated and the system to be treated which surrounds the reaction space can be simultaneously the system to be treated.

The use of a reactor as reaction space is preferred.

According to a preferred embodiment of the present invention, the reaction space is a component of a mobile device which consists of a piston-like tube in which the reaction space is situated, and wherein this mobile device has a reaction space outlet and feed lines for the reactants and optionally dilution water. The mobile device, preferably the piston-like tube, with the reaction space is conducted and moved into a guide channel, preferably a cylindrical outer tube, which tube, which is shut off by a shutoff element from the pipe having the system to be treated, has access to the pipe having the system to be treated. After introduction of the mobile device, preferably the piston-like tube having the reaction space into the guide channel, preferably the cylindrical outer tube, the shutoff element can be opened and the mobile device, preferably the piston-like tube having the reaction space can be introduced into the pipe having the system to be treated. Preferably, the feed lines for the reactants and optionally dilution water are conducted from the top into the mobile device and the reaction space. Likewise, structures are possible in which the feed lines are conducted outside the reaction space, preferably the reactor, to the inlet of the reaction space, for example, from the side or from the bottom.

Moreover, it is possible, in the process of the present invention, to deliver the $ClO_2$, which is formed into the system and which is to be treated without diversions or other additional lines, directly from the reaction space in which the $ClO_2$ is formed since the outlet is situated directly at the end of the reaction space, preferably the reactor, and is therefore surrounded by the system to be treated. Preferably, the reaction space is situated in the main pipe of the system to be treated and not in a bypass line to the main line which can be spatially isolated by means of shutoff elements situated upstream and downstream of the site lying in the bypass line for feeding chlorine dioxide to the system to be treated. This measure is the preferred variant of the method. The renewal rate of the system to be treated at the outlet of the reaction space, preferably the reactor outlet, can be affected by the mass flow rate of the system to be treated and the geometrical ratios in the pipe. If the reaction space outlet is situated, for example at the effluent side of the system to be treated at the reaction space, vortices generating reduced pressure form, which vortices accelerate the distribution of the chlorine dioxide generated in the system to be treated.

The reaction space, preferably the reactor, is preferably operated without a pressure control appliance. Via a free outlet at the end of the reaction space, preferably the reactor, it is ensured that the pressure in the reaction space can only increase up to the value which is exerted on the reaction space by the surrounding system to be treated.

The concentration of the chlorine dioxide formed in the reaction space, preferably in the reactor, can be set, in combination with pressure and temperature of the surrounding system to be treated, in such a manner that the solubility limit of chlorine dioxide in the system to be treated is not exceeded. As a result, the formation of a 2-phase system, due to a forming of a chlorine dioxide gas phase, can be prevented.

The pressure ratios for a reactor used in a pipe can be affected, for example by shutoff elements integrated into the pipe. Furthermore, fittings situated in the pipe can modify the turbulence of the flow of the system to be treated and can thereby modify the distribution of the added chlorine dioxide in the system to be treated.

If the system to be treated at the outlet of the reaction space, preferably the reactor, is renewed at a corresponding rate, the concentration of the chlorine dioxide solution leaving the reaction space, preferably the reactor, can be abruptly shifted to a milligram range.

In principle, all chemical methods of producing $ClO_2$ in the reaction space can be employed, in particular the methods 1 to 3 described above and/or methods starting from chlorate.

Preference in the present invention is given to the hydrochloric acid-chlorite method 1. In this method the starting chemicals (reactants) of alkali metal chlorite salt, preferably sodium chlorite, can be present in aqueous solutions of 3.5% to 40%. The acid is preferably hydrochloric acid in a concentration of 3.5% to 42%.

In a particularly preferred embodiment of the present invention, use is made of concentrated starting chemicals and the hydrochloric acid chlorite method 1 is employed. The concentration of the hydrochloric acid is about 33-42% and that of the sodium chlorite solution is about 25-40%. The starting chemicals are not diluted before or in the reaction space.

The starting chemicals (reactants), in particular acid and chlorite, are passed into the reaction space as aqueous solution, as described above, separately by inherent pressure of the solutions or using pumps, and brought to reaction.

In the preferred procedure, the reactants are used as concentrated solutions and the use of dilution water is dispensed with, and so the chlorine dioxide concentration at the end of the reaction space, preferably at the reactor outlet, or the outlet line, is set to greater than 80 g/l of solution. Alternatively, dilution water can be used in order to set the chlorine dioxide concentration at the end of the reaction space, preferably at the reactor outlet, or at the outlet line, to be greater than 3 g/l of solution, preferably greater than 26 g/l of solution, and, particularly preferably, greater than 80 g/l of solution.

The device/apparatus for carrying out the method according to the present invention typically includes one or more tanks for the starting chemicals (reactants), in particular an acid storage tank and a chlorite storage tank, wherein an aqueous acid solution can be stored in the acid storage tank and a solution of an alkali metal salt of a chlorite ion can be stored in the chlorite storage tank. Apparatuses can be provided which not only can feed the suitable components into the storage tanks but can also take off solutions. Preferably, these apparatuses include pumps and feed lines which are sufficient to ensure the flow rates of the starting chemicals (reactants), in particular of aqueous acid solutions and solutions of alkali metal salts of a chlorite ion, and also of dilution water rate. Specialists in the field can readily determine suitable sizes for the relevant storage tanks, feed lines and pumps in order to achieve the required feed rates of reactant solutions (e.g., aqueous acid solutions, solutions of an alkali metal salt of a chlorite ion).

The device can have at least two pumps for two starting chemicals (reactants), but in particular one for the solution of the alkali metal salt of a chlorite ion and another for the aqueous acid solution.

The device can further comprise an apparatus for mixing the solution of the starting chemicals (reactants), in particular the solution which contains the alkali metal salt of a chlorite ion and the aqueous acid solution, in order to provide an aqueous reaction solution of the starting chemicals (reactants). Any apparatus which mixes the abovementioned solutions adequately can be used, including conventional T pieces or other connection elements which combine two streams or three streams to form one combined stream, throttle lines and/or a stirred tank. The aqueous reaction solution can then be fed after mixing into the reaction space. Preferably, the two reactants and the optionally used dilution water are mixed in the reaction space. The mixing operation can be introduced by any appliance, such as baffle plates, injectors or packings, which ensures optimum mixing.

As reaction space, use can be made of any reactor which is able to initiate the reaction between the starting chemicals (reactants), in particular the aqueous acid solution and the alkali metal salt of a chlorite ion, for example, simple tanks, mass-flow or plug-flow reactors and tubular reactors. Of these, a tubular reactor is particularly preferred. Usually, a chlorine dioxide generation unit consists of only one tubular reactor, but the generation output of a unit can be increased by the parallel arrangement of a plurality of reactors, for example to form a tube bundle. The reactor can be not only temperature-controlled, but also consist of a good heat-conducting material in order to deliver liberated heat of reaction to the surrounding system to be treated. The material of which the reactor is fabricated can consist of materials which exhibit good stability to the respective reaction solutions. In the generation of chlorine dioxide solutions having concentrations of greater than 28 g/l, the reaction material can be, for example, titanium, alloy 31, glass or chemistry materials (e.g., polymers such as PVDF or PTFE). When titanium is used as reactor material, the reaction solutions are fed in such a manner that when hydrochloric acid is used, this does not come into contact with the titanium surface without the reaction partner which in this case is an oxidizing agent (e.g. sodium chlorite) being present simultaneously. This procedure prevents titanium corrosion since the corrosion-triggering property of the hydrochloric acid is abolished under oxidizing conditions. This state can be achieved, e.g., by feeding the hydrochloric acid via a plastic line into the centre of the reactor—at the greatest possible distance from the titanium surface—and the oxidizing reaction partner being situated close to the hydrochloric acid feed point. The $ClO_2$ is conducted away from the reactor by any desired mechanism which is able to remove an aqueous solution from a reactor. Preferably, the reaction is carried out continuously, and $ClO_2$ is continuously removed from the reactor. After it leaves the reactor, the $ClO_2$ can be metered directly into the system to be treated.

A tubular reactor is preferably used according to the present invention. Generally the tube of the tubular reactor is constructed in such a manner that it has a sufficient length to ensure sufficient residence time in the reactor in order that the components react sufficiently in view of the flow rate of the reaction solution, its concentration of reactants and the temperature of the reaction solution. A particularly preferred reactor which can be used for producing a suitable generator of aqueous chlorine dioxide on site is a tubular reactor which contains one or more tube coils. Specialists in the field are able to vary the size and shape of the reactor as a function of the amount of aqueous chlorine dioxide to be produced, the flow rate and concentration of reactants, the pH of the aqueous reaction solution, the pH of the $ClO_2$ and the temperature of the reactor. Specialists in the field are likewise able to modify the temperature of the reactor appropriately.

The reaction time in the reaction space can vary. With increasing concentration of the reactants in the reaction space, the optimum of the residence time can decrease. If a solution having a chlorine dioxide concentration of 20 g/l is produced, the median reactor residence time is about 60 minutes to 4 minutes, preferably approximately 4 to 6 minutes, in order to achieve a yield of approximately 85%. If the chlorine dioxide concentration according to the particularly preferred embodiment increases to greater than 80 g/l, the median reactor residence time is about 0.1 minute to 1.5 minutes, preferably 0.3 to 0.6 minute, particularly preferably approximately 0.4 minute, for a 95% yield. The minimum of the median residence time can be achieved when the reactants are used as concentrated solutions, dilution water is not used and the necessary stoichiometric excess of acid or chlorine is minimized. If in the method according to the invention the reactor is designed for a certain generation rate (e.g., 10 kg/h), surprisingly this gives the possibility of increasing the amount of chlorine dioxide generated by more than threefold. Although this high flexibility of generation rate is accompanied in the case of relatively large generation rates with a decrease in conversion rate (e.g., 10 kg/h=95% yield; 30 kg/h=80% yield), especially for such applications considerable advantages result in which considerable increases of the standard required rates of chlorine dioxide result temporarily and at low frequency.

The chlorine dioxide solution leaving the reaction space outlet can be diluted in such a manner that the renewal rate of the system to be treated at the reaction space outlet is about 0.1 $m^3$/h to 20 $m^3$/h per gram and hour of chlorine dioxide generated, preferably 1 $m^3$/h to 4 $m^3$/h per gram and hour of chlorine dioxide generated.

The method according to the invention can be carried out, for example, using the devices depicted in FIG. 1 and FIGS. 2a and 2b.

FIG. 1 shows an outline structure for carrying out the method having a reaction space in a pipe without the mobile device and without being restricted to certain starting chemicals (reactants) or embodiments. The units having the stated numbers may therefore be used correspondingly generally in their function for all methods having the various possible starting chemicals (reactants) and easily recognizable to those skilled in the art.

In FIG. 1, the device for treating water and aqueous systems in pipes with chlorine dioxide consists of two tanks for the starting chemicals (reactants), in particular a chlorite storage tank 1 having feed pump 4 and an acid storage tank 2 having feed pump 5. The water pump 6 is supplied via the water connection 3. All three feed pumps are connected via individual lines to the bottom side of the reaction space, preferably reactor, 7. In the reaction space, preferably the reactor, there are situated appliances of the prior art which ensure rapid complete mixing of the components fed in the reaction space. By varying the concentration contents of the reactant solutions or the amount of dilution water used, the concentration of the resultant chlorine dioxide solution is set to greater than 3 g/l, preferably greater than 26 g/l, and particularly preferably to greater than 80 g/l. The preferred variant, however, is to allow the reactants to react in the reaction space without dilution by water (i.e., dilution water feed pump 6 switched off).

At the top, opposite end, of the reaction space 7, preferably the reactor, there is situated the reaction space outlet 8.

A preferred device for the method according to the present invention is reproduced in FIG. 2a (maintenance state) and FIG. 2b (operating state). In this case it is essential to the invention that the reaction space, preferably the reactor, is situated in a mobile device 14, preferably a piston-like tube 14, and wherein this mobile device possesses a reaction space outlet and feed lines for the reactants and optionally dilution water, and can be slid and moved by the movement device 16, preferably a threaded rod, into the guide channel 13, preferably a cylindrical outer tube 13. In this case the shutoff element 12 is closed and so no system to be treated can penetrate into the interior of the guide channel 13. After the mobile device 14 has been introduced into the guide channel 13 using the movement device 16 (FIG. 2a, maintenance state), the shutoff element 12 can be opened without the system to be treated being able to exit from the guide channel 13. Using the movement device 16, the mobile device 14 and therewith the reaction space, preferably the reactor, situated therein, can then be introduced into the system-bearing pipe 11 (FIG. 2b, operating state). The surface between the guide channel 13 and the mobile device 14 is designed in such a manner that it is not permeable to the system to be treated 9. The sealing systems used are either component of the guide channel 13, the mobile device 14, or they are present in both components. In principle, all sealing variants are suitable which prevent the escape of system to be treated 9 from the pipe 11 via the guide channel 13 into the open. Via the feed lines 15 the reactants are transported into the reaction space, preferably the reactor. The passages of the feed lines 15 into the reaction space, preferably the reactor, are constructed in such a manner that even at relatively high pressures, sealing of these passages is provided.

Preferably, the feed lines 15 are conducted from the top into the mobile device 14 and into the reaction space. Likewise, for example, structures are possible in which the feed lines for the reactants are conducted outside the reaction space, preferably the reactor, for entry of the reaction space, such as from the side or from the bottom. The mobile appliance 14 having the reaction space, preferably the reactor, can also be constructed in such a manner that it is arranged in an additional outer tube. All process modes are possible which can prevent escape of the system to be treated from the pipe 11 and can simultaneously enable the introduction of the reaction space into this pipe. Preferably, the reaction space, preferably the reactor, is a closed space in which the reaction space outlet is situated at the opposite end of the reactant feed line 15. Preferably, the reaction space outlet is formed by bore holes in the reaction space wall and the mobile device 14 is positioned in the pipe 11 in such a manner that the reaction space outlet is situated at the top. The chlorine dioxide formed can be delivered to the system to be treated 11 via the reaction space outlet. Preferably, the chlorine-dioxide-treated system 10 leaves the pipe section in which the chlorine dioxide solution is added to the system to be treated 9. By varying the reaction space outlet (size, type and number of orifices), position of the reaction space outlet to the direction of flow of the system to be treated, and also by various positioning of the reaction space outlet with respect to the open diameter of the pipe 11, various distribution patterns of the chlorine dioxide generated in the system to be treated 9 can be set in the pipe 11.

In all cases, the preferred variant is maximum reduction of the volume of the reaction space, preferably the reactor. By using concentrated reactants, in this preferred variant the concentration of the chlorine dioxide solution at the reaction space outlet 8 is set to greater than 80 g/l.

The guide channel 13 is preferably mounted on the system-bearing pipe 11 in a 12 o'clock or 6 o'clock position. Regardless of the site of installation of the guide channel 13, the reaction space, preferably the reactor, should preferably be arranged in such a manner that it is situated below relative to the reaction space outlet. The advantage is that gaseous components can leave the reaction space.

A preferred variant comprises allowing the reactants to react in the reaction space without dilution by water (dilution water feed pump 6 switched off). In this case the concentration of the resultant solution at the reaction space outlet 8 can increase to greater than 9 g/l, preferably greater than 26 g/l, and particularly preferably to greater than 80 g/l of chlorine dioxide per litre. In this preferred variant it is advantageous to reduce the reactor volume maximally. Generally, no further appliances are necessary to achieve the renewal rate of the system to be treated 9 at the reaction space outlet 8 in order to shift the concentration of the chlorine dioxide solution after entry into the system to be treated 9 rapidly from preferably greater than 80 g per litre to the milligram region. Likewise, it is generally not difficult to set the pressure of the system to be treated 9 in the pipe 11 in such a manner that the solubility limit of the chlorine dioxide in the aqueous solution in the reaction space 7, preferably the reactor, as shown in FIG. 3, is not exceeded.

FIGS. 2a and 2b show an outline structure for carrying out the method according to the invention without being restricted to defined embodiments or starting chemicals (reactants). The units having the specified number are therefore to be employed in their function correspondingly generally for all methods having the various possible starting chemicals (reactants) and may be readily recognized by those skilled in the art.

Figure 3:
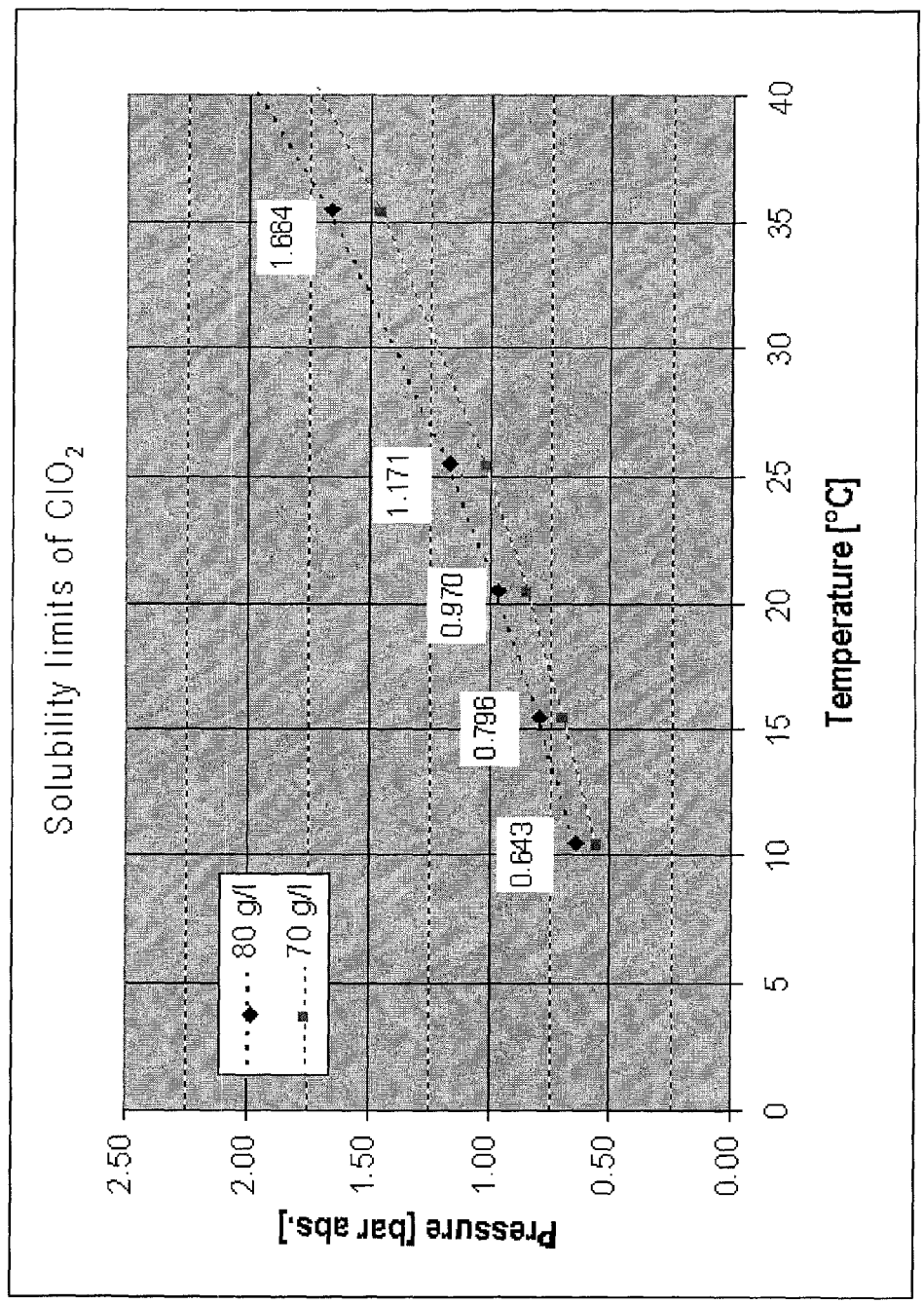
FIG. 3 illustrates the solubility limits of chlorine dioxide in an aqueous solution as a function of pressure and temperature.

FIG. 3 shows the solubility limits of chlorine dioxide in an aqueous solution as a function of pressure and temperature, by way of example for the chlorine dioxide concentrations 70 g/l and 80 g/l.

EXAMPLES

Having generally described the present invention above, a further understanding can be obtained by reference to certain specific examples which are provided herein for purposes of illustration only, and are not intended to be limiting unless otherwise specified.

Example 1

The device described in FIGS. 2a and 2b was used. The mobile device 14 having the reactor 7 contained therein was situated with shutoff element 12 open in the pipe 11 through which the system flowed and was thereby in the operating state. The pipe 11 had a diameter of 600 mm and the system to be treated 9 in the pipe 11 was surface water which was fed at a mass flow rate of 1000 m$^3$/h via pipe 11 to a treatment unit. The pressure in the pipe 11 was 6.2 bar. Via the feed lines 15, 5.9 l of a 25% strength sodium chlorite solution and 5.3 litres of a 32% strength hydrochloric acid solution were fed per hour to the reactor. The reactor had a free volume of 0.075 litre and the residence time of the reaction mixture in the reaction space was 0.4 minute. 11.1 litres of chlorine dioxide solution having a content of 92 g/l were delivered per hour via the reaction space outlet 8 into the system to be treated 9 (surface water) flowing round the reactor 7. This corresponded to a calculated chlorine dioxide concentration of 1 mg/l. At an acid excess of 300%, the chlorine dioxide was generated at a yield of 95%. The content of chlorine dioxide in the system to be treated 9 (surface water) was reduced to a concentration of 0.2 mg/l at the inlet of the water treatment plant which was approximately 1 km away from the chlorine dioxide metering site.

The invention claimed is:

1. A method of treating an aqueous stream flowing in a pipe with chlorine dioxide (ClO$_2$), comprising:
    providing a moveable reactor contained in a piston-like tube in a guide channel;
    opening a shutoff valve between the pipe and the guide channel without the aqueous stream flowing in the pipe exiting the guide channel;
    introducing the reactor into the aqueous stream flowing in the pipe via the guide channel;
    generating chlorine dioxide in the moveable reactor situated in the aqueous stream in the pipe;
    delivering the chlorine dioxide generated in the reactor to the aqueous stream in the pipe, and
    removing the reactor from the aqueous stream in the pipe via the guide channel.

2. The method of claim 1, wherein the reactor is removed from the aqueous stream in the pipe and subsequently introduced back into the aqueous stream in the pipe independently of the pressure state of the pipe.

3. The method of claim 1, wherein the reactor is a tubular reactor.

4. The method of claim 1, wherein a reaction time between the chlorine dioxide and components in the aqueous stream in the pipe is from 4 to 60 minutes.

5. The method of claim 1, wherein the chlorine dioxide is generated from a reaction between an alkali metal chlorite salt and hydrochloric acid.

6. The method of claim 1, wherein the chlorine dioxide is generated from a reaction between sodium chlorite and hydrochloric acid.

7. The method of claim 6, wherein the sodium chlorite is an aqueous solution of 3.5% to 40% sodium chlorite.

8. The method of claim 6, wherein the hydrochloric acid is in a concentration from 3.5% to 42%.

9. The method of claim 1, wherein the chlorine dioxide is generated from reactants comprising sodium chlorite and chlorine.

10. The method of claim 1, wherein dilution water is introduced into the reactor.

11. The method of claim 1, wherein no dilution water is introduced into the reactor.

12. The method of claim 1, wherein chlorine dioxide solution leaving the reactor is diluted such that a renewal rate at an outlet of the reactor is about 0.1 m$^3$/h to 20 m$^3$/h per gram of chlorine dioxide generated.

13. The method of claim 1, wherein the chlorine dioxide formed in the reactor is passed out of the reactor directly into the aqueous stream in the pipe, and the concentrations of one or more starting chemicals is selected such that the concentration, at a reactor outlet, of the chlorine dioxide formed in the reactor is greater than 3 g/l of solution.

14. The method of claim 6, wherein the concentration of the hydrochloric acid is 33-42% and that of the sodium chlorite solution is 25-40%.

15. The method of claim 6, wherein the reactor comprises a titanium surface, and reaction solutions are fed into the reactor such that the hydrochloric acid does not come into contact with the titanium surface without the sodium chlorite being present.

16. The method of claim 1, wherein the reactor and guide channel are situated on a main pipe of a system to be treated and not on a bypass line of the main pipe.

17. The method of claim 1, wherein the guide channel is a cylindrical outer tube.

\* \* \* \* \*